(12) United States Patent
Flatters et al.

(10) Patent No.: US 12,733,940 B2
(45) Date of Patent: Sep. 15, 2026

(54) ACETABULAR REAMER HANDLE AND METHOD OF REAMING AN ACETABULUM

(71) Applicant: DEPUY IRELAND UNLIMITED COMPANY, Ringaskiddy (IE)

(72) Inventors: Ian Flatters, Sheffield (GB); David Horne, Leeds (GB); Duncan Temple, London (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 93 days.

(21) Appl. No.: 16/968,712

(22) PCT Filed: Jan. 10, 2019

(86) PCT No.: PCT/EP2019/050571
§ 371 (c)(1),
(2) Date: Aug. 10, 2020

(87) PCT Pub. No.: WO2019/161986
PCT Pub. Date: Aug. 29, 2019

(65) Prior Publication Data

US 2020/0375614 A1 Dec. 3, 2020

(30) Foreign Application Priority Data

Feb. 21, 2018 (GB) ...................................... 1802787

(51) Int. Cl.
*A61B 17/16* (2006.01)

(52) U.S. Cl.
CPC ...... *A61B 17/1666* (2013.01); *A61B 17/1631* (2013.01)

(58) Field of Classification Search
CPC ............ A61B 17/1631; A61B 17/1633; A61B 17/1666; A61B 17/164; A61B 17/0281; A61B 17/0218
See application file for complete search history.

(56) References Cited

U.S. PATENT DOCUMENTS 7,008,430 B2 3/2006 Dong et al.
7,637,909 B2 12/2009 Lechot et al.
(Continued)

FOREIGN PATENT DOCUMENTS

CN 103690227 B 1/2018
EP 2954860 A2 12/2015
(Continued)

OTHER PUBLICATIONS

EP Search Report for PCT/EP2019/050571 mailed Apr. 12, 2019.
(Continued)

*Primary Examiner* — Amy R Sipp
(74) *Attorney, Agent, or Firm* — Barnes & Thornburg LLP

(57) ABSTRACT

An acetabular reamer handle and a method of reaming an acetabulum. The handle includes a hollow shaft having a plurality of shaft sections including a distal shaft section having a distal end and a proximal end and an additional shaft section having a distal end that is pivotally attached to the proximal end of the distal shaft section to allow the additional shaft section and the distal shaft section to be adjustably oriented at an angle. The handle also includes a hollow neck part having a longitudinal axis. The handle further includes a drive line having a head part mounted for rotation about the longitudinal axis and connectable to a reamer. A distal end of the distal shaft section is pivotally attached to a proximal end of the neck part to allow the distal shaft section and the neck part to be adjustably oriented at an angle.

19 Claims, 7 Drawing Sheets

(56) References Cited

U.S. PATENT DOCUMENTS

| | | | | |
|---|---|---|---|---|
| 8,052,690 | B2 | 11/2011 | Berthusen et al. | |
| 9,066,730 | B2 | 6/2015 | McMinn et al. | |
| 9,572,683 | B2 | 2/2017 | Roose | |
| 2004/0097947 | A1 | 5/2004 | Wolford | |
| 2005/0159751 | A1* | 7/2005 | Berthusen | A61B 17/1666 606/80 |
| 2007/0073302 | A1* | 3/2007 | Myers | A61B 17/1633 606/80 |
| 2012/0109229 | A1 | 5/2012 | Forsell | |

FOREIGN PATENT DOCUMENTS

| | | | |
|---|---|---|---|
| JP | 2005523764 | A | 11/2005 |
| JP | 2008529701 | A | 8/2008 |
| WO | 2003/065905 | A1 | 8/2003 |
| WO | 2003065906 | A3 | 11/2003 |
| WO | WO 2018/033788 | A1 | 2/2018 |

OTHER PUBLICATIONS

Japanese Search Report from corresponding Japanese Patent Application No. JP2020-544281, dated Jan. 10, 2023, 2 pages.
Indian Search Report from corresponding Indian Patent Application No. 202017035466, dated May 24, 2022, 6 pages.
New Zealand Examination Report from corresponding New Zealand Patent Application No. 767417, dated Jan. 29, 2024, 4 pages.
Chinese Examination Report from corresponding Chinese Patent Application No. 20198001473.7, dated Dec. 22, 2023, 6 pages.
Australian Search Report for corresponding Australian Patent Application No. 2019225764, dated Nov. 8, 2023, 4 pages.
Great Britain Search Report for corresponding GB Patent Application No. GB1802787.0 dated Aug. 20, 2018, 4 pages.

* cited by examiner 10
40
40A
40B
42
44
45
48A
48B
50
51
52
80
150
151
152
82
34
60
20B
76B
21B
20
9A
72B
9B
77
74B
20A
62
8A
8B
8C
7
6
64
74A
72A
21A
76A 34
60
66
20B
82
152
9A
150
20
170
9B
20A
26
10
80
8B
52
8C
50
70
8A
6
44
42
46

ACETABULAR REAMER HANDLE AND METHOD OF REAMING AN ACETABULUM

This application is a National Stage Application filed Under 35 U.S.C. § 371 of International Application No. PCT/EP2019/050571 filed Jan. 10, 2019, which claims priority to GB1802787.0 filed Feb. 21, 2018, which are both hereby incorporated by reference in their entireties.

FIELD OF THE INVENTION

This invention relates to an acetabular reamer handle. This invention also relates to a method of reaming an acetabulum in a hip replacement procedure.

BACKGROUND OF THE INVENTION

Hip replacement is a surgical procedure in which the hip joint is replaced by a prosthetic implant. As part of a hip replacement procedure, an acetabulum of the patient may be prepared for receiving an acetabular cup implant by reaming it to an appropriate size and depth. A surgical tool for reaming the acetabulum may include a reamer having a substantially hemispherical dome to be received in the acetabulum. The reamer may also include features located on an outer surface of the dome for grating the inner surface of the acetabulum as the reamer rotates. The reamer may be attached to a distal end of a tubular reamer handle, to allow the surgeon to manipulate it (e.g. to position the dome within the acetabulum and to apply a force for pressing the reamer against the inner surface of the acetabulum as the reamer rotates). A driveline may extend within the reamer handle for transmitting torque to the reamer.

Various kinds of reamer handles may be used.

One kind of reamer handle is an offset reamer handle. This kind of reamer handle may include a pair of bends in the tube, forming a dog-leg configuration, which may allow a surgeon to work more easily around soft tissue.

Another kind of reamer handle may include a single bend.

A further kind of reamer handle may be substantially straight (i.e. including no bends).

WO2003/065906 describes a surgical device for holding and rotating an acetabular reaming head. The device comprises a shaft having a length which runs from a first end adapted for holding an acetabular reaming head to a second end. At least part of the shaft is divergent from the axis defined by the first and second ends of the shaft, for example the shaft may include a C-shaped divergent portion. A head held by the device can therefore access the acetabulum in its true anatomical position while avoiding encroachment of the shaft on surrounding body parts.

Surgeons may prefer to use one or more of the above mentioned types of reamer handle in a hip replacement procedure according to the approach that is being followed and/or according to the surgeon's personal preference. To accommodate this, a surgical kit may typically include one of each kind of reamer handle. In any given procedure, it is possible that one or more of the reamer handles in the kit may go unused, in which case the cost and weight of the surgical kit has been increased unnecessarily. Even if more than one kind of reamer handle is used during a procedure, it may be inconvenient and time consuming to switch between them.

U.S. Pat. No. 8,052,690 describes an orthopaedic reamer driver that includes a tubular housing having at least one first positioning feature. A driveshaft within the housing has a drive end. A variable angle cap is pivotally coupled with the housing adjacent the drive end. The variable angle cap includes at least one leg extending along a side of the housing. Each leg has a second positioning feature selectively engaging and disengaging with a corresponding first positioning feature at a selected one of a plurality of angular positions. Each second positioning feature maintains the variable angle cap at the selected angular position when engaged with the corresponding first positioning feature. A variable angle joint is coupled to the drive end, and a reamer drive head is coupled to the variable angle joint.

U.S. Pat. No. 7,008,430 describes a positioning tool for a joint socket cutting instrument or a implant that is designed for use with a minimally invasive surgical procedure and in conjunction with a computer assisted surgical procedure. The positioning tool has a longitudinally extending drive shaft having a moveable joint at a first end and a drive coupling for connecting to a power source at a second end. A holder for mounting a cutting tool such a drill or as an acetabular cutting instrument or for mounting an acetabular implant is coupled to the moveable joint at the first end of the drive shaft for movement with respect to the drive shaft. The holder is rotatable about a central axis thereof when the drive shaft is rotated. The drive shaft includes a shaft bearing mounted thereon which is pivotally coupled to the shaft at a fixed longitudinal position and is pivotally coupled to a longitudinally extending first arm having a handle. A tracker system which is capable of being utilized by a computer-aided surgical system is mounted on the first arm. A second arm is provided which is pivotally connected to the holder at a first end and pivotally connected to the first arm at a second end. The resulting four bar linkage allows the holder and the cutting instrument/implant to be manipulated in any position while the known geometric relationship between the tracker and the holder allows the location of the holder to be displayed by the computer on a cathode ray tube with respect to a joint.

WO 2018/033788 A1 describes a surgical reamer driver device that provides a fully closed tube which prevents the invasion of debris and minimizes abrasion of soft tissue during use. The reamer device includes a minimum number of component assemblies, so as to permit easy replacement and minimize wear. The surgical reamer driver has a housing assembly in a stand-alone, assembled unit, a transmission drive train in a stand-alone, assembled unit enclosed in the housing assembly, and having at least one double universal joint and a surgical tool connector at the distal end thereof, a motor shaft coupling in a stand-alone, assembled unit at the proximal end thereof, and a handle assembly in a stand-alone, assembled unit at the proximal end thereof, these four basic components forming a driver which in a fully assembled state effectively prevents debris from access in the inner workings of the driver. A method for disassembling the reamer driver includes the steps of: a. actuating a sliding release sleeve to unlock the handle assembly from the housing assembly, thereby permitting the de-encapsulation of the drive train within the housing assembly; b. sliding the handle assembly off of the housing thereby effectively de-encapsulating the drive train; c. pulling the motor shaft coupling out of the housing thereby freeing the drive train from axial constraint on one end; d. unsnapping the drive train on the one end and lifting the one end out of the housing assembly thereby permitting removal of the drive train; and e. pulling the drive train out of the housing assembly, thus removing the drive train from the housing assembly.

US 2004/097947 A1 describes an orthopaedic reamer assembly for minimally invasive surgery including a reamer and a driver. The driver includes a shaft with a distal end and a longitudinal axis; and a driver head connected to the distal end. The driver head is pivotable about an axis generally perpendicular to the longitudinal axis. The reamer is connected to the driver head.

EP 2 954 860 A2 describes an orthopaedic reamer handle, comprising: a reamer portion configured to transmit torque to a reamer head; a driver portion connected to said reamer portion and configured to receive and transmit torque from a driver; and a drive train connecting said reamer portion and said driver portion and configured to transmit torque from said driver portion to said reamer portion, said drive train including: a first drive shaft having a first end and a second end, said first end being connected to said driver portion, said first drive shaft defining a first axis; a first intermediate connector having a first intermediate end and a second intermediate end, said first intermediate end being connected to said second end; an offsetting member having a third end and a fourth end, said third end being connected to said second intermediate end at an acute angle relative to said first axis, said offsetting member defining a second axis; and a second intermediate connector connecting said fourth end to said reamer portion at an acute angle relative to said second axis.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided an acetabular reamer handle comprising:

- a hollow shaft having a plurality of shaft sections comprising:
  - a distal shaft section having a distal end and a proximal end; and
  - an additional shaft section having a distal end that is pivotally attached to the proximal end of the distal shaft section to allow the additional shaft section and the distal shaft section to be adjustably oriented at an angle relative to each other;
- a hollow neck part having a longitudinal axis;
- a driveline extending through the shaft and the neck part, wherein a head part of the driveline is mounted for rotation about the longitudinal axis of the neck part and is connectable to an acetabular reamer,
- wherein a distal end of the distal shaft section is pivotally attached to a proximal end of the neck part to allow the distal shaft section and the neck part to be adjustably oriented at an angle relative to each other.

The provision of the plurality of shaft sections and the neck part that are pivotally attached together for orientation at angles relative to each other can allow the acetabular reamer handle to adopt a plurality of different configurations. For instance, by appropriate angling of the neck part, the distal shaft section and the additional shaft section, the acetabular reamer handle may operate either as an offset reamer handle, as a reamer handle including a single bend and/or as a substantially straight reamer handle having no bends in it. This can allow the functionality of different kinds of acetabular reamer handles to be provided using a single tool. This can reduce the cost, weight and cleaning time of a surgical kit incorporating the acetabular reamer handle. Also, the configuration of the acetabular reamer handle may be altered conveniently during a procedure, which may avoid the need to switch between different kinds of acetabular reamer handle.

The acetabular reamer handle may include a distally facing engagement surface located at the distal end of the distal shaft section and a plurality of engagement surfaces located at the proximal end of the neck part. The neck part may be pivotable with respect to the distal shaft section to present each one of the plurality of engagement surfaces to the distally facing engagement surface located at the distal end of the distal shaft section to orient the neck part and the distal shaft section at a respective angle relative to each other. The provision of the plurality of engagement surfaces located at a proximal end of the neck part may allow the surgeon to conveniently select a predetermined angle for the neck part relative to the distal shaft section (e.g. 0°, +30°, −30°, +45°, −45°, +60°, −60° . . . etc.) by selectively engaging one of the plurality of engagement surfaces with the distally facing engagement surface located at the distal end of the distal shaft section.

The distally facing engagement surface of the distal shaft section may be provided on an engagement member. The engagement member may be resiliently biased distally to urge the distally facing engagement surface of the distal shaft section against one of the plurality of engagement surfaces located at a proximal end of the neck part to resist relative movement between the neck part and the distal shaft section. The biasing of the engagement member in this way can serve to retain the orientation of the neck part relative to the distal shaft section during use.

The engagement member may be proximally retractable along a longitudinal axis of the distal shaft section for disengaging the distally facing engagement surface of the distal shaft section from an engagement surface located at a proximal end of the neck part, to allow the neck part to pivot freely with respect to the distal shaft section. This can allow the surgeon to release the neck part, so as to freely pivot the neck part while selecting an orientation between the neck part and the distal shaft section. The engagement member may include a gripping surface for allowing a surgeon to manually operate the engagement member.

The engagement member may be substantially tubular. The driveline may pass through a centre of the engagement member. The engagement member may be provided as a sleeve on an outer surface of the distal shaft section. This arrangement for the engagement member is relatively compact. It is also envisaged that the engagement member may be provided at least partially inside the distal shaft section.

The distally facing engagement surface located at the distal end of the distal shaft section may be substantially ring shaped.

The distally facing engagement surface and each of the plurality of engagement surfaces located at the proximal end of the neck part may be substantially flat. This can avoid the need for complicated and intricate arrangements for fixing the orientation of the neck part relative to the distal shaft section.

The driveline may include at least one of: a universal joint located at the pivot point between the distal end of the distal shaft section and the proximal end of the neck part; and a universal joint located at the pivot point between the distal end of the additional shaft section and the proximal end of the distal shaft section. This can allow an angling of the distal shaft section relative to the neck part and/or an angling of the additional shaft section relative to the distal shaft section to be accommodated.

The attachment between the distal shaft section and the additional shaft section may be configured similarly to the attachment between the neck part and the distal shaft section.

The acetabular reamer handle may include a distally facing engagement surface located at the distal end of the additional shaft section and a plurality of engagement surfaces located at a proximal end of the distal shaft section, wherein the distal shaft section is pivotable with respect to the additional shaft section to present each one of the plurality of engagement surfaces of the distal shaft section to the distally facing engagement surface located at the distal end of the additional shaft section to orient the distal shaft section and the additional shaft section at a respective angle relative to each other. The provision of the plurality of engagement surfaces located at a proximal end of the distal shaft section may allow the surgeon to conveniently select a predetermined angle for the distal shaft section relative to the additional shaft section (e.g. 0°, +30°, −30°, +45°, −45°, +60°, −60° . . . etc.) by selectively engaging one of the plurality of engagement surfaces with the distally facing engagement surface located at the distal end of the additional shaft section.

The distally facing engagement surface of the additional shaft section may be provided on an engagement member. The engagement member of the additional shaft section may be resiliently biased distally to urge the distally facing engagement surface of the additional shaft section against one of the plurality of engagement surfaces located at the proximal end of the distal shaft section to resist relative movement between the distal shaft section and the additional shaft section. The biasing of the engagement member of the additional shaft section in this way can serve to retain the orientation of the distal shaft section relative to the additional shaft section during use.

The engagement member of the additional shaft section may be proximally retractable along a longitudinal axis of the additional shaft section for disengaging the distally facing engagement surface of the additional shaft section from an engagement surface located at a proximal end of the distal shaft section, to allow the distal shaft section to pivot freely with respect to the additional shaft section. This can allow the surgeon to release the distal shaft section, so as to freely pivot the distal shaft section while selecting an orientation between the distal shaft section and the additional shaft section. The engagement member of the additional shaft section may include a gripping surface for allowing a surgeon to manually operate the engagement member of the additional shaft section.

The engagement member of the additional shaft section may be substantially tubular. The driveline may pass through a centre of the engagement member of the additional shaft section. The engagement member of the additional shaft section may be provided as a sleeve on an outer surface of the additional shaft section. This arrangement for the engagement member of the additional shaft section is relatively compact. It is also envisaged that the engagement member of the additional shaft section may be provided at least partially inside the distal shaft section.

The distally facing engagement surface located at the distal end of the additional shaft section may be substantially ring shaped.

The distally facing engagement surface located at the distal end of the additional shaft section and each of the plurality of engagement surfaces located at the proximal end of the distal shaft section may be substantially flat. This can avoid the need for complicated and intricate arrangements for fixing the orientation of the distal shaft section relative to the additional shaft section.

The distal end of the additional shaft section and the proximal end of the distal shaft section may be pivotally attached to allow the additional shaft section and the distal shaft section to be adjustably oriented at an angle relative to each other only within a first plane, and the distal end of the distal shaft section may be pivotally attached to the proximal end of the neck part to allow the distal shaft section and the neck part to be adjustably oriented at an angle relative to each other only in the first plane.

The shaft may comprise two shaft sections. The additional shaft section may be a proximal shaft section of the shaft.

The shaft may include more than two shaft sections. The additional shaft section may be an intermediate shaft section and the shaft may include one or more further pivotally connected shaft sections arranged proximally of the intermediate shaft section. This may provide additional flexibility, for example to work around soft tissue in the incision site.

In one embodiment, the includes a plurality of shaft sections comprising: said distal shaft section; said additional shaft section forming a first intermediate shaft section of the shaft; a further shaft section forming a second intermediate shaft section, wherein a distal end of the second intermediate shaft section is pivotally attached to a proximal end of the first intermediate shaft section; and a further shaft section forming a proximal shaft section of the shaft, wherein a distal end of the proximal shaft section is pivotally attached to a proximal end of the second intermediate shaft section. This can allow the acetabular reamer handle to adopt a substantially C-shaped configuration, with the longitudinal axis of the neck part oriented substantially parallel to a longitudinal axis of the proximal shaft section of the shaft.

According to another aspect of the invention, there is provided a surgical kit comprising the acetabular reamer handle set out above and one or more differently sized acetabular reamers connectable to the head part of the driveline of the acetabular reamer handle.

According to a further aspect of the invention, there is provided a method of reaming an acetabulum of a patient, the method comprising:

- connecting a reamer to a head part of a driveline of an acetabular reamer handle, the acetabular reamer handle comprising:
  - a hollow shaft having a plurality of shaft sections comprising:
    - a distal shaft section having a distal end and a proximal end; and
    - an additional shaft section having a distal end that is pivotally attached
  - to the proximal end of the distal shaft section;
  - a hollow neck part having a longitudinal axis; and
  - the driveline,
  - wherein the driveline extends through the shaft and the neck part, wherein the head part is mounted for rotation about the longitudinal axis of the neck part, and wherein a distal end of the distal shaft section is pivotally attached to a proximal end of the neck part,
- orienting the neck part and the distal shaft section at a first angle relative to each other;
- orienting the additional shaft section and the distal shaft section at a second angle relative to each other; and
- operating the driveline to apply torque to the reamer while the reamer is located in the acetabulum of the patient.

By appropriate orientation of the neck part, the distal shaft section and the additional shaft section, the acetabular reamer handle may to adopt a plurality of different configurations. For instance, the acetabular reamer handle may operate either as an offset reamer handle, as a reamer handle including a single bend and/or as a substantially straight reamer handle having no bends in it. This can allow the functionality of different kinds of acetabular reamer handles to be provided using a single tool. This can reduce the cost, weight and cleaning time of a surgical kit incorporating the acetabular reamer handle. Also, the configuration of the acetabular reamer handle may be altered conveniently during a procedure, which may avoid the need to switch between different kinds of acetabular reamer handle.

Orienting the neck part and the distal shaft section at the first angle relative to each other may include pivoting the neck part to present one of a plurality of engagement surfaces located at a proximal end of the neck part with a distally facing engagement surface located at the distal end of the distal shaft section. The provision of the plurality of engagement surfaces located at a proximal end of the neck part may allow the surgeon to conveniently select a predetermined angle for the neck part relative to the distal shaft section (e.g. 0°, +30°, −30°, +45°, −45°, +60°, −60° . . . etc.) by selectively engaging one of the plurality of engagement surfaces with the distally facing engagement surface located at the distal end of the distal shaft section.

The distally facing engagement surface of the distal shaft section may be provided on an engagement member. The engagement member may be resiliently biased distally to urge the distally facing engagement surface of the distal shaft section against one of the plurality of engagement surfaces located at the proximal end of the neck part to resist relative movement between the neck part and the distal shaft section. The method may further include manually retracting the engagement member in a proximal direction to disengage the distally facing engagement surface of the distal shaft section from one of the engagement surfaces located at the proximal end of the neck, to allow the neck part to pivot freely with respect to the distal shaft section. This can allow the surgeon to release the neck part, so as to freely pivot the neck part while selecting an orientation between the neck part and the distal shaft section.

Orienting the additional shaft section and the distal shaft section at the second angle relative to each other may include pivoting the distal shaft section to present one of a plurality of engagement surfaces located at a proximal end of the distal shaft section with a distally facing engagement surface located at the distal end of the additional shaft section. The provision of the plurality of engagement surfaces located at a proximal end of the distal shaft section may allow the surgeon to conveniently select a predetermined angle for the distal shaft section relative to the additional shaft section (e.g. 0°, +30°, −30°, +45°, −45°, +60°, −60° . . . etc.) by selectively engaging one of the plurality of engagement surfaces with the distally facing engagement surface located at the distal end of the additional shaft section.

The distally facing engagement surface of the additional shaft section may be provided on an engagement member. The engagement member may be resiliently biased distally to urge the distally facing engagement surface of the additional shaft section against one of the plurality of engagement surfaces located at the proximal end of the distal shaft section to resist relative movement between the additional shaft section and the distal shaft section. The method may further include manually retracting the engagement member of the additional shaft section in a proximal direction to disengage the distally facing engagement surface of the additional shaft section from one of the engagement surfaces located at the proximal end of the distal shaft section, to allow the additional shaft section to pivot freely with respect to the distal shaft section. This can allow the surgeon to release the distal shaft section, so as to freely pivot the distal shaft section while selecting an orientation between the distal shaft section and the additional shaft section.

The method may include orienting the additional shaft section and the distal shaft section at the first angle relative to each other within a first plane, and orienting the distal shaft section and the neck part at the second angle relative to each other in the first plane.

The first angle may be equal and opposite to the second angle within the first plane. This can allow the neck part to be oriented parallel to the additional shaft section during reaming.

BRIEF DESCRIPTION OF THE D WINGS

Embodiments of the present invention will be described hereinafter, by way of example only, with reference to the accompanying drawings in which like reference signs relate to like elements and in which.

DETAILED DESCRIPTION

Figure 1A:
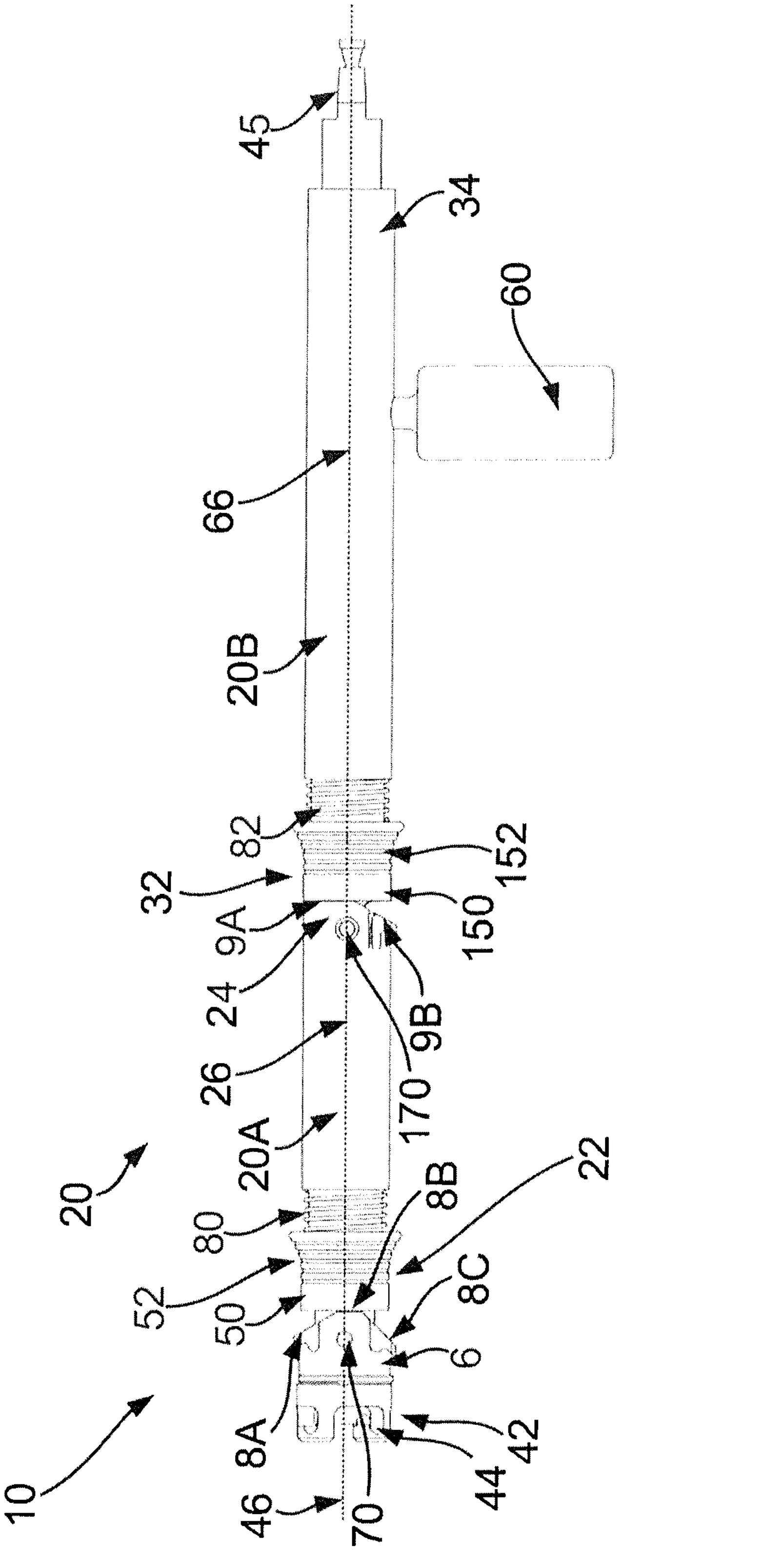
FIG. 1A shows a side view of an acetabular reamer handle according to an embodiment of this invention.

Embodiments of the present invention are described in the following with reference to the accompanying drawings.

FIGS. 1 to 5 show a number of different views of an acetabular reamer handle 10 according to an embodiment of this invention.

The acetabular reamer handle 10 includes a shaft 20. As can be seen in the cross section of FIG. 5, the shaft 20 is substantially hollow. The shaft includes a plurality of shaft sections. The shaft sections may be substantially cylindrical and may have a substantially circular cross section. In the present embodiment, these shaft sections include a distal shaft section 20A and an additional shaft section 20B. In the present embodiment, the shaft 20 includes only two shaft sections, whereby the additional shaft section 20B may be considered to be a proximal shaft section. It is envisaged that the shaft 20 may include more than two (e.g. three, four . . . ) shaft sections including a distal shaft section 20A of the kind shown in FIGS. 1 to 5, an additional shaft section 20B of the kind shown in FIGS. 1 to 5 (in which case the additional shaft section 20B may be considered to be an intermediate shaft section) and one or more further shaft sections. Each further shaft section(s) in such embodiments may be configured similarly to the additional shaft section 20B of the kind shown in FIGS. 1 to 5 and may be connected in sequence, proximally with respect to the additional shaft section 20B. These further shaft section(s) may include a proximal shaft section located at a proximal end of the hollow shaft 20, and optionally one or more intermediate shaft sections located intermediate the additional shaft section 20B and the aforementioned proximal shaft section.

Each shaft may be generally elongate and cylindrical in shape. Each shaft section has a distal end and a proximal end. For instance, in the present embodiment, the distal shaft section 20A has a distal end 22 and a proximal end 24, and the additional shaft section 20B includes a distal end 32 and a proximal end 34.

One or more handle parts 60 may be provided on the shaft 20 to facilitate holding the acetabular reamer handle 10 and to allow an axial force to be applied by a surgeon, for urging a reamer attached to the distal end of the acetabular reamer handle 10 into the inner surface of the acetabulum of a patient during reaming. As shown in FIGS. 1 to 5, each handle part 60 may extend radially outward from the side of one of the shaft sections of the shaft 20. In the present embodiment, the acetabular reamer handle 10 includes a single handle part 60, which extends radially outward from the side of the additional shaft section 20B.

The acetabular reamer handle 10 also includes a neck part 6. The neck part 6 is substantially hollow. The neck part may be substantially cylindrical and may have a substantially circular cross section. The neck part 6 has a proximal end 62 and a distal end 64 and a longitudinal axis 46. Each shaft section also has a longitudinal axis. In the present embodiment, the distal shaft section 20A has a longitudinal axis 26 and the additional shaft section has a longitudinal axis 66.

As will be described in more detail below, the proximal end 62 of the neck part 6 is pivotally connected to the distal end 22 of the distal shaft section 20A and the proximal end 24 of the distal shaft section 20A is pivotally connected to the distal end 32 of the additional shaft section 20B. In embodiments where further shaft sections are included, each further shaft section may be connected in a sequence proximally with respect to the additional shaft section 20B, using a pivotal connection and locking mechanism of the kind to be described below in relation to the pivotal connection and locking mechanism between the distal shaft section 20A and the additional shaft section 20B.

The acetabular reamer handle 10 also includes a driveline 40. The drive line 40 is shown in full in the exploded view of FIG. 4 and parts of the drive line 40 are also visible in FIGS. 1 to 3. For the purposes of clarity, only a head part 42 (to be described below) of the driveline 40 is shown in the cross section of FIG. 5. The driveline 40 is elongate and dimensioned to fit inside and extend through the hollow shaft 20 and neck part 6.

The driveline 40 may include a plurality of driveline sections. In the present embodiment, these driveline sections include a distal driveline section 40A and an additional driveline section 40B. In the present embodiment, the additional driveline section 40B may be considered to be a proximal driveline section. In general, the driveline 40 may include a respective driveline section for each shaft section of the hollow shaft 20. To accommodate any pivoting of the shaft sections and neck part 6 with respect to each other, the driveline 40 may include universal joints positioned along its length, to coincide with the pivotal connections between the various shaft sections and the neck part 6. In the present embodiment, the driveline 40 includes a first universal joint 48A joining a proximal end of the head part 42 of the drive line 40 to a distal end of the distal driveline section 40A and a second universal joint 48B connecting a proximal end of the distal driveline section 40A to a distal end of the additional driveline section 40B.

The proximal end 34 of the proximal shaft section of the acetabular reamer handle 10 (which is formed by the additional shaft section 20B in the present embodiment having two shaft sections) may have an opening through which a proximal end 45 of the driveline 40 may protrude. The proximal end 45 of the driveline 40 may include connection features for connection to a power tool such as a rotational driver for applying torque to the driveline 40. In use, the driveline 40 rotates to transmit the torque through the hollow shaft 20 and neck part 6 to the distally located head part 42 of the drive line 40. The head part 42 of the drive line 40 is connectable to a reamer 100. FIG. 1B shows a side view of the acetabular reamer handle 10 of FIG. 1A, with an acetabular reamer 100 connected to the head part 42 of the driveline 40. To implement the connection between the head part 42 and the acetabular reamer 100, the head part 42 may include distally located connection features 44 for connection with corresponding connection features of the acetabular reamer 100. As shown in FIG. 1B, the acetabular reamer 100 may, for instance comprise a hemispherical dome 102 for insertion into the acetabulum of a patient. An outer surface of the dome 102 may include features 104 for grating bone away from the inner surface of the acetabulum as the acetabular reamer 100 rotates with the driveline 40.

The head part 42 is mounted for rotation about the longitudinal axis 46 of the neck part 6. The axis of rotation of the head part 42 may generally be coaxial with the longitudinal axis 46. In the present example, a proximal end of the head part 42 is located inside the neck part 6. An outer surface of the head part 42 (e.g. of the proximal end of the head art in the present embodiment) may form a snug fit with an inner surface of the neck part 6, so that the head part 42 rides within the neck part 6, to maintain the coaxial relationship between the axis of rotation of the head part 42 and the longitudinal axis 46. In the present embodiment, the distal end of the head part 42 protrudes distally from the distal end 62 of the neck part 6 and includes the aforementioned connection features 44 for connection to an acetabular reamer. The distal end 64 of the head part 42 may be generally cylindrical and may have a larger diameter than the proximal end of the head part 42, which rotates within the neck part 6. In this embodiment, the distal end of the head part 42 has the same outer diameter as the distal end 62 of the neck part 6, so that the distal end of the head part 42 is flush with the outer surface of the distal end 62 of the neck part 6.

The shaft sections may be of different lengths (as measured along their longitudinal axes). For instance, in the present embodiment, the distal shaft section 20A is shorter than the additional shaft section 20B. The head part 42 may be shorter (as measured along its longitudinal axis 46) than the shaft sections.

As mentioned previously, the proximal end 62 of the neck part 6 is pivotally connected to the distal end 22 of the distal shaft section 20A and the proximal end 24 of the distal shaft section 20A is pivotally connected to the distal end 32 of the additional shaft section 20B.

Figure 4:
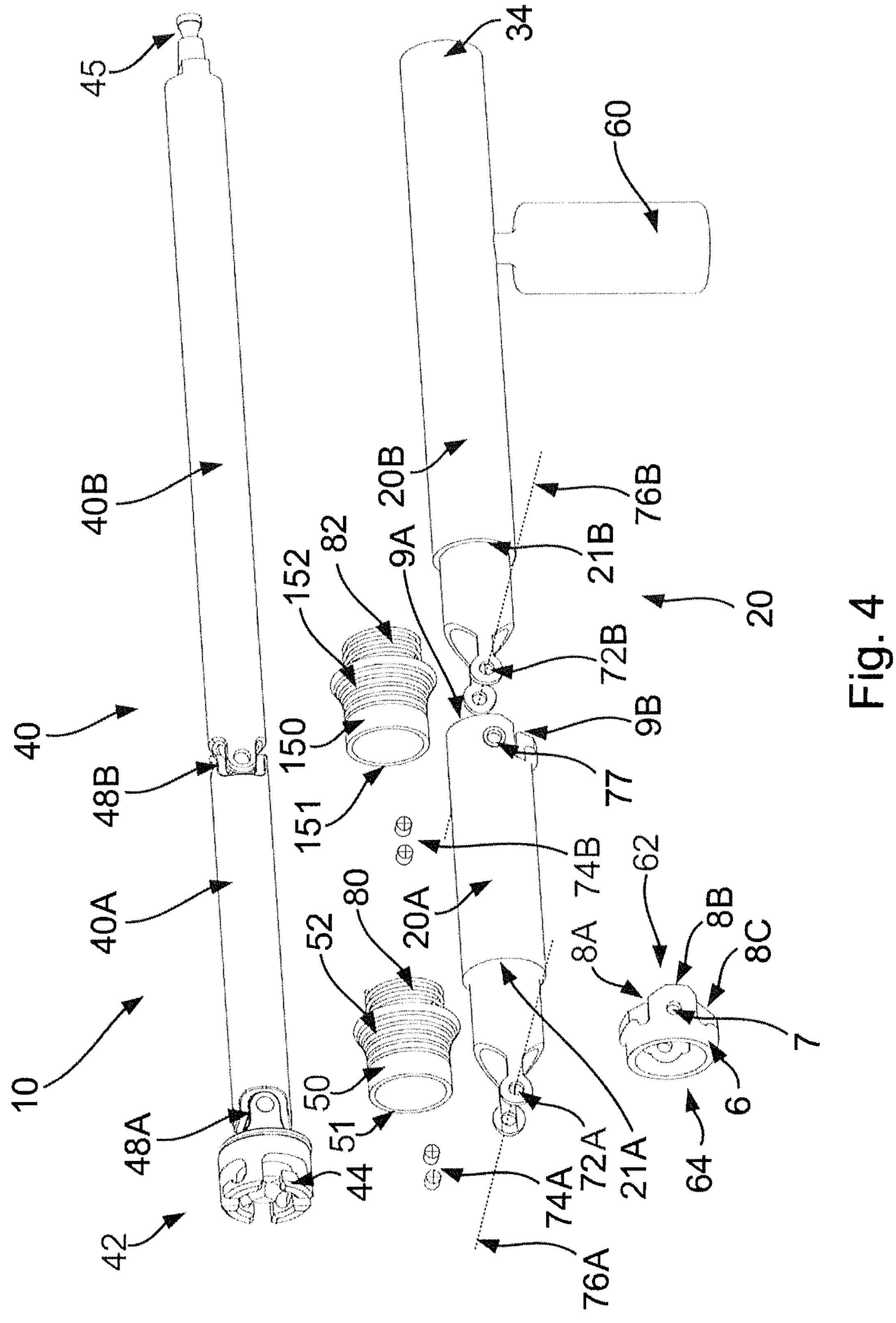
FIG. 4 shows an exploded view of the acetabular reamer handle of FIG. 1A.
Figure 5:
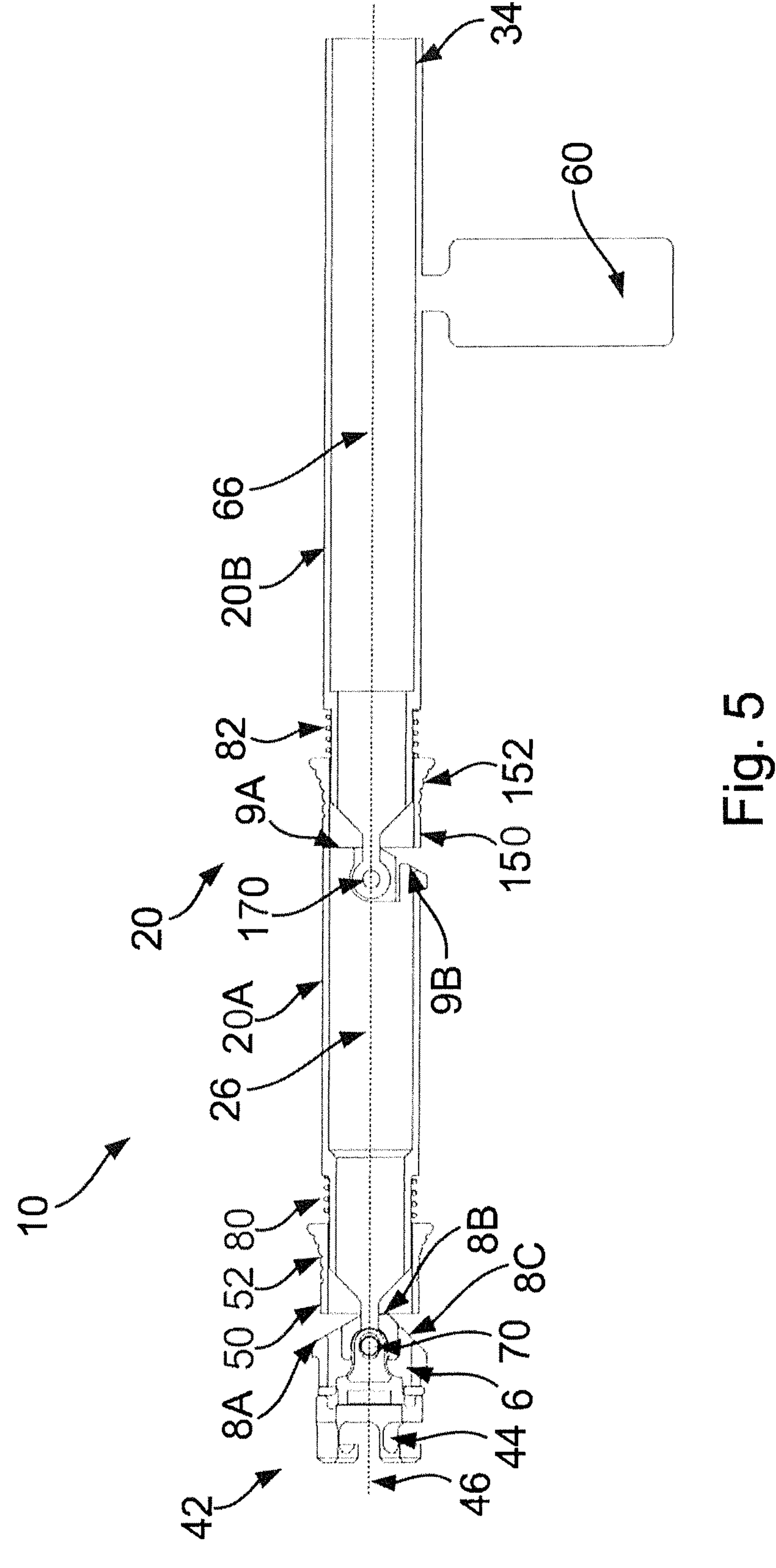
FIG. 5 shows a cross section of the acetabular reamer handle of FIG. 1A.

The pivotal connection 70 between the proximal end 62 of the neck part 6 and the distal end 22 of the distal shaft section 20A in this embodiment is formed by a pair of holes 72A located at the distal end 22 of the distal shaft section 20A and a pair of corresponding holes 7 located on the neck part 7, through which bolts 74A pass. The axis of rotation 76A provided by the pivotal connection 70 is generally perpendicular to both the longitudinal axis 46 of the neck part 6 and the longitudinal axis 26 of the distal shaft section 20A. As shown in FIG. 4, the holes 72A may be located at the ends of a pair arms that extend distally from the end of the distal shaft section 20A. These arms can provide clearance between the hollow cylindrical part of the distal shaft section 20A and the proximal end 62 of the neck part 6, to allow the neck part 6 to rotate about the pivotal connection 70.

The pivotal connection 170 between the proximal end 24 of the distal shaft section 20A and the distal end 32 of the additional shaft section 20B in this embodiment is formed by a pair of holes 72B located at the distal end 32 of the additional shaft section 20B and a pair of corresponding holes 77 located at the proximal end 24 of the distal shaft section 20A, through which bolts 74B pass. The axis of rotation 76B provided by the pivotal connection 170 is generally perpendicular to both the longitudinal axis 26 of the distal shaft section 20A the longitudinal axis 66 of the additional shaft section 20B. As shown in FIG. 4, the holes 72B may be located at the ends of a pair arms that extend distally from the end of the additional shaft section 20B. These arms can provide clearance between the hollow cylindrical part of the distal shaft section 20B and the proximal end 24 of the distal shaft section 20A, to allow the distal shaft section 20A to rotate about the pivotal connection 170.

The pivotal connections 70, 170 can allow the neck part 6, the distal shaft section 20A and the additional shaft section 20B to be adjustably oriented at angles relative to each other. This can allow the acetabular reamer handle 10 to adopt a plurality of different configurations. There are several common surgical approaches for total hip arthroplasty (THA), for example, direct anterior, anterior-lateral, posterior-lateral, posterior, direct superior, and multi-incision approaches. A surgeon's choice of handle configuration may be based on the surgical approach used, their handle preference, and the patient's anatomy.

Figure 3:
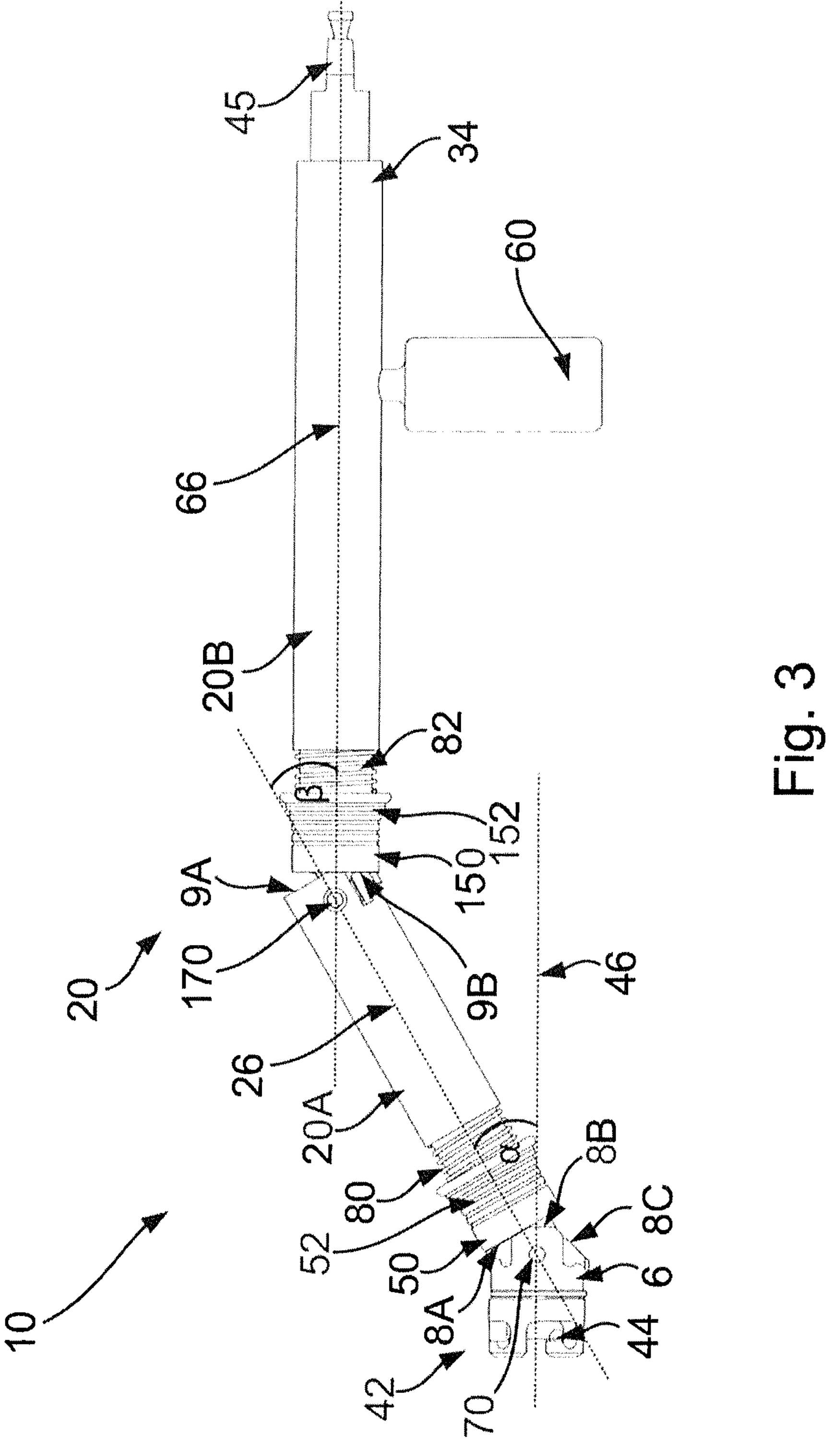
FIG. 3 shows a further side view of the acetabular reamer handle of FIG. 1A.

For instance, by appropriate angling of the neck part 6, the distal shaft section 20A and the additional shaft section 20B, the acetabular reamer handle 10 may operate as an offset reamer handle, as demonstrated in FIG. 3. In this configuration, the neck part 6 is angled about the pivotal connection 70 such that the longitudinal axis 46 of the neck part 6 is oriented at a non-zero angle $\alpha$ with respect to the longitudinal axis 26 of the distal shaft section 20A. The angle may, for instance, be in the range $30° \leq \alpha \leq 60°$. Note that the neck part 6 may pivot in either direction. Similarly, the distal shaft section 20A is angled about the pivotal connection 170 such that the longitudinal axis 26 of the distal shaft section 20A is oriented at a non-zero angle $\beta$ with respect to the longitudinal axis 66 of the additional shaft section 20B. Typically, the angle $\beta$ for adopting a offset reamer handle configuration may be equal in size to the angle $\alpha$. Accordingly, the angle $\beta$ may, for instance, also be in the range $30° \leq \beta \leq 60°$. As can be seen in FIG. 3 though, the angle $\beta$ for adopting a offset reamer handle configuration is generally in the opposite direction to the angle $\alpha$. By way of example only, offset reamer handles are often used in hip replacement procedures in which the posterior-lateral approach is used.

Figure 2:
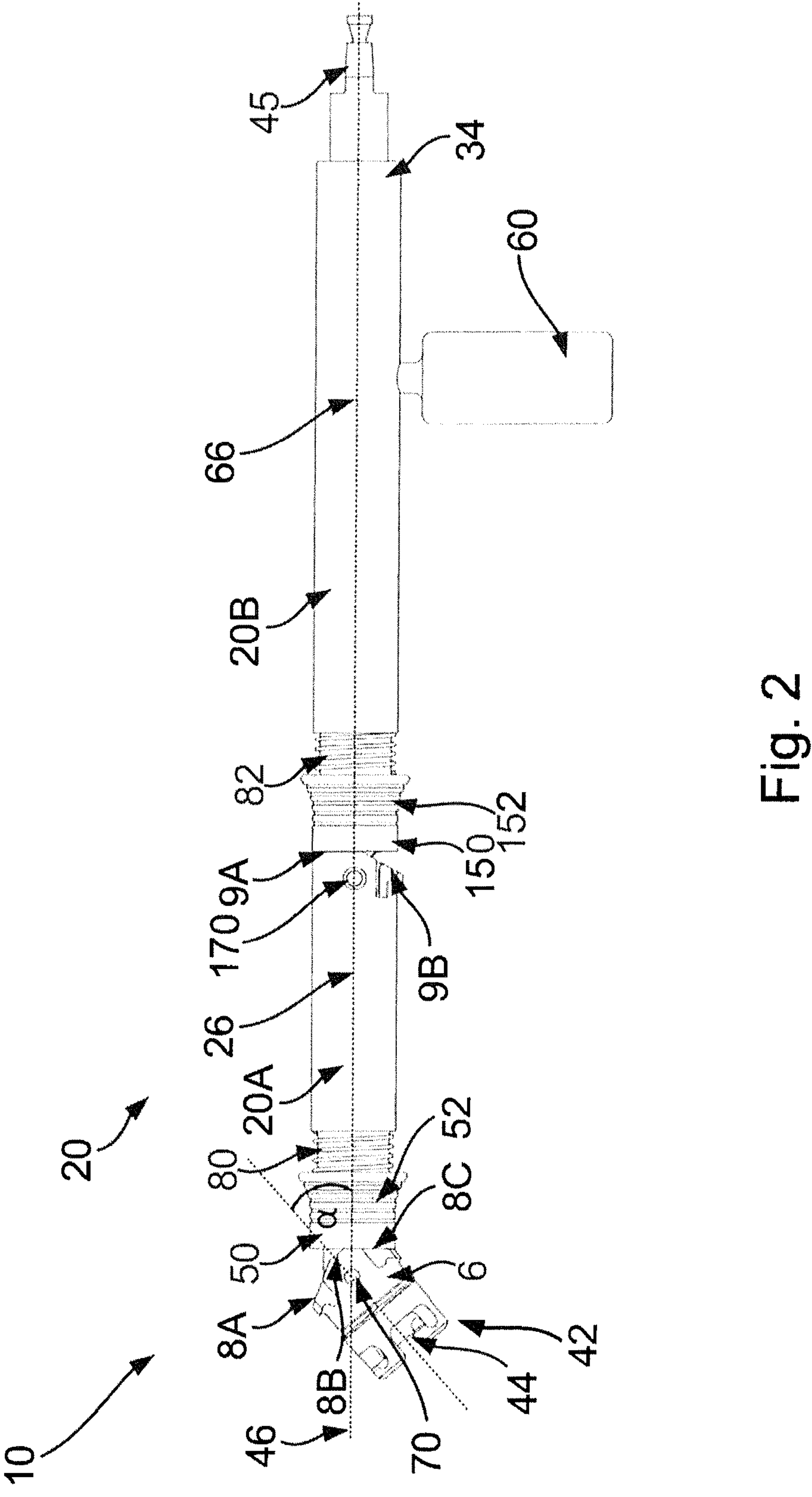
FIG. 2 shows another side view of the acetabular reamer handle of FIG. 1A.

In another example, the acetabular reamer handle 10 may operate a reamer handle including a single bend, as demonstrated in FIG. 2. In this configuration, the longitudinal axes 26, 66 of the distal shaft section 20A and the additional shaft section 20B are aligned to be parallel, while the neck part 6 is angled about the pivotal connection 70 such that the longitudinal axis 46 of the neck part 6 is oriented at a non-zero angle $\alpha$ with respect to the longitudinal axis 26 of the distal shaft section 20A. The angle $\alpha$ may, for instance, be in the range $30° \leq \alpha \leq 60°$. Again, note that the neck part 6 may pivot in either direction. By way of example only, reamer handles including a single bend are often used in hip replacement procedures in which the anterior approach is used.

Figure 1B:
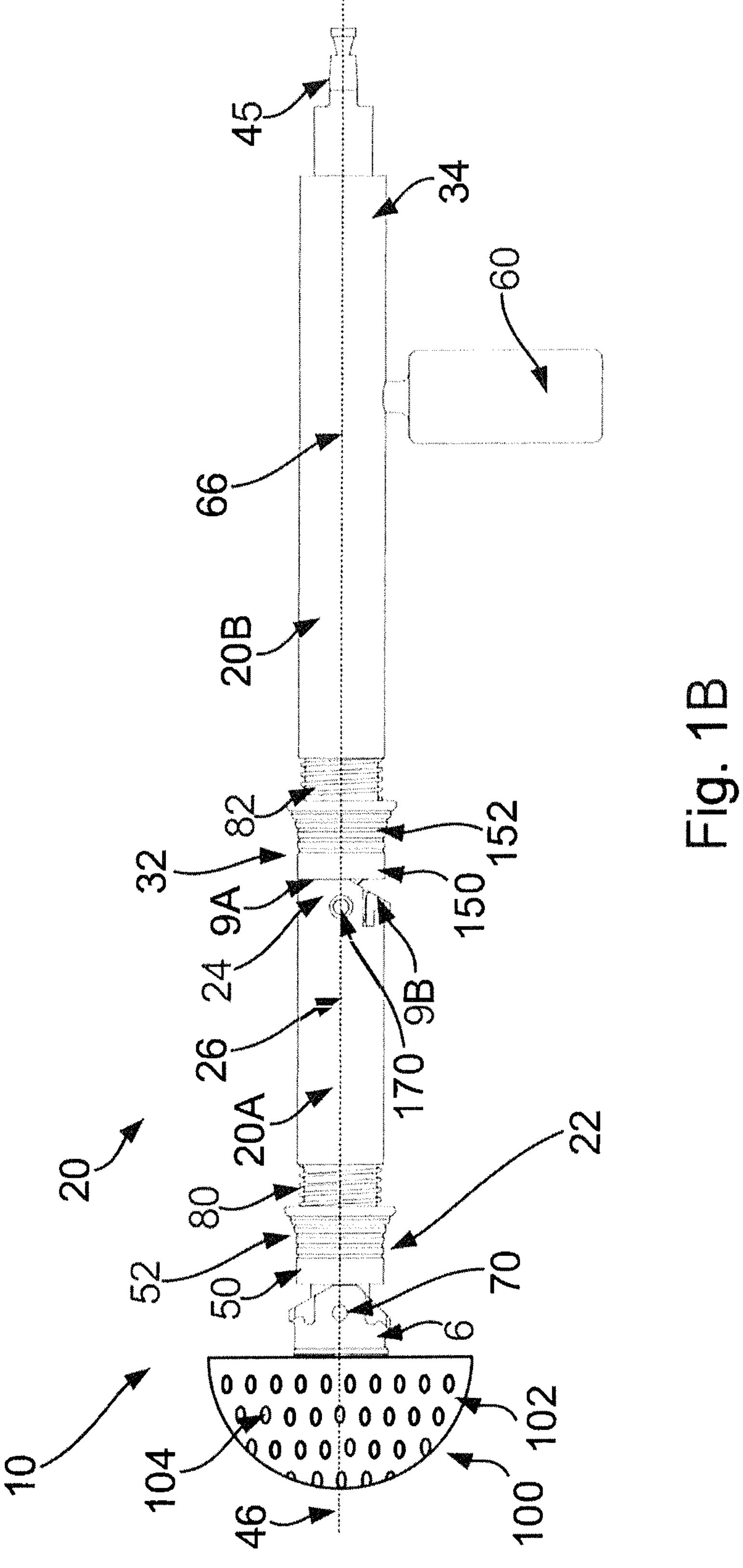
FIG. 1B shows a side view of the acetabular reamer handle of FIG. 1, with an acetabular reamer connected to a distally located head part of a driveline of the acetabular reamer handle.

In a further example, the acetabular reamer handle 10 may operate a straight reamer handle including no bends, as demonstrated in FIGS. 1A and 1B. In this configuration, the longitudinal axes 46, 26, 66 of the neck part 6, the distal shaft section 20A and the additional shaft section 20B are aligned to be parallel ($\alpha = \beta = 0$). By way of example only, straight reamer handles are often used in hip replacement procedures in which the posterior-lateral approach is used.

This can allow the functionality of different kinds of acetabular reamer handles to be provided using a single tool. This can reduce the cost, weight and cleaning time of a surgical kit incorporating the acetabular reamer handle. Also, the configuration of the acetabular reamer handle may be altered conveniently during a procedure, which may avoid the need to switch between different kinds of acetabular reamer handle.

In this embodiment, the axes of rotation 76A, 76B of the pivotal connections 70, 170 are substantially parallel. Although this is not considered to be essential, it can allow the traditional configuration of an offset reamer handle to be adopted. In particular, when the acetabular reamer handle 10 adopts the offset reamer handle configuration, the axes 46, 26, 66 of the neck part 6, distal shaft section 20A and additional shaft section 20B are all contained in the same plane.

Note that the universal joint 48A of the driveline 40 is positioned to coincide with the pivotal connection 70 between the proximal end 62 of the neck part 6 and the distal end 22 of the distal shaft section 20A. In particular, the universal joint 48A may be located at the intersection between the axes and 46, 26, and 76A. This can allow the above described angling of the neck part 6 relative to the distal shaft section 20A to be accommodated. Similarly, the universal joint 48B of the driveline 40 is positioned to coincide with the pivotal connection 170 between the proximal end 24 of the distal shaft section 20A and the distal end 32 of the additional shaft section 20B. In particular, the universal joint 48B may be located at the intersection between the axes and 26, 66, and 76B. This can allow the above described angling of the distal shaft section 20A relative to the additional shaft section 20B to be accommodated.

One or more of the pivotal connections 70, 170 of the acetabular reamer handle 10 may include a locking mechanism for keeping the relative orientations of the neck part 6 and various shaft sections fixed while the acetabulum of the patient is being reamed.

In this embodiment, the pivotal connection 70 is provided with a locking mechanism that includes an engagement member 50 having a substantially ring shaped engagement surface 51. The engagement member 50 is located at the distal end 22 of the distal shaft section 20A. The engagement member 50 may be substantially tubular and may be mounted as a sleeve on an outer surface of the distal shaft section 20A. The driveline 40 may pass through a centre of the engagement member 50.

The locking mechanism in this embodiment also includes a spring, such as a helical spring 80. The helical spring 80 may be may be located in between the engagement member 50 and a circumferential lip 21A on the outer surface of the distal shaft section 20A. The spring (e.g. the helical spring 80) is arranged to bias the engagement member 50 distally.

In use, the engagement surface 51 of the engagement member 50 is urged against the proximal end 62 of the neck part 6 by the spring of the locking mechanism, which resists pivotal movement of the neck part 6 relative to the distal shaft section 20A.

In this embodiment, the proximal end 62 of the neck part 6 is provided with a plurality of engagement surfaces 8A, 8B, 8C. The engagement surfaces 8A, 8B, 8C and the engagement surface 51 may be substantially flat, so as to provide stable and secure contact between them. The neck part 6 is pivotable about the pivotal connection 70 to present each one of the plurality of engagement surfaces 8A, 8B, 8C to the engagement surface 51 of the engagement member. This can allow the neck part 6 to be retained at an angle to the distal shaft section 20A corresponding to the angle between the surface normal of the chosen engagement surface 8A, 8B, 8C and the longitudinal axis 46 of the neck part 6. This approach can allow a number of discrete, predetermined angles (e.g. 0°, +30°, −30°, +45°, −45°, +60°, −60° . . . etc.) between the neck part 6 and the distal shaft section 20A to be provided for. For instance, in the present embodiment:

- the engagement surface 8A can be engaged with the engagement surface 51 of the engagement member 50 to angle (and retain) the longitudinal axis 46 of the neck part 6 at +30° to the longitudinal axis 26 of the distal shaft section 20A (see FIG. 3);
- the engagement surface 8B can be engaged with the engagement surface 51 of the engagement member 50 to angle (and retain) the longitudinal axis 46 of the neck part 6 parallel to (i.e. at 0°) to the longitudinal axis 26 of the distal shaft section 20A (see FIG. 1A); and
- the engagement surface 8C can be engaged with the engagement surface 51 of the engagement member 50 to angle (and retain) the longitudinal axis 46 of the neck part 6 at −30° to the longitudinal axis 26 of the distal shaft section 20A (see FIG. 2).

Although the present example includes three engagement surfaces 8A, 8B, 8C, it is envisaged that a different number of such surfaces may be provided.

To release the engagement surface 51 from the proximal end 62 of the neck part 6, the engagement member 50 may be retracted in a proximal, axial direction, against the bias provided by the spring 80. The engagement member 50 may include a gripping surface 52 for assisting the surgeon to retract the engagement member 50 manually. When the proximal end 62 (e.g. one of the engagement surfaces 8A, 8B, 8C) is released from the engagement surface 51 by retraction of the engagement member 50, the neck part 6 is able freely to pivot about the pivotal connection 70. The surgeon may then angle the neck part 6 as desired (e.g. by presenting a different one of the engagement surfaces 8A, 8B, 8C to the engagement surface 51) and then release the engagement member 50 so that the engagement surface 51 re-engages with the proximal end 62 of the neck part 6 under the bias provided by the spring 80.

In this embodiment, the pivotal connection 170 is provided with a locking mechanism that is similar to the one described above in relation to the locking mechanism of the pivotal connection 70. The locking mechanism of the pivotal connection includes an engagement member 150 having a substantially ring shaped engagement surface 151. The engagement member 150 is located at the distal end 32 of the additional shaft section 20B. The engagement member 150 may be substantially tubular and may be mounted as a sleeve on an outer surface of the distal shaft section 20B. The driveline 40 may pass through a centre of the engagement member 150.

The locking mechanism in this embodiment also includes a spring, such as a helical spring 82. The helical spring 82 may be may be located in between the engagement member 150 and a circumferential lip 21B on the outer surface of the additional shaft section 20B. The spring (e.g. the helical spring 82) is arranged to bias the engagement member 150 distally.

In use, the engagement surface 151 of the engagement member 150 is urged against the proximal end 24 of the distal shaft section 20A by the spring 82 of the locking mechanism, which resists pivotal movement of the distal shaft section 20A relative to the additional shaft section 20B.

In this embodiment, the proximal end 24 of the distal shaft section 20A is provided with a plurality of engagement surfaces 9A, 9B. The engagement surfaces 9A, 9B and the engagement surface 151 may be substantially flat, so as to provide stable and secure contact between them. The distal shaft section 20A is pivotable about the pivotal connection 170 to present each one of the plurality of engagement surfaces 9A, 9B to the engagement surface 151 of the engagement member. This can allow the distal shaft section 20A to be retained at an angle to the additional shaft section 20B corresponding to the angle between the surface normal of the chosen engagement surface 9A, 9B and the longitudinal axis 26 of the distal shaft section. This approach can allow a number of discrete, predetermined angles (e.g. 0°, +30°, −30°, +45°, −45°, +60°, −60° . . . etc.) between the distal shaft section 20A and the additional shaft section 20B to be provided for. For instance, in the present embodiment:

- the engagement surface 9A can be engaged with the engagement surface 151 of the engagement member 150 to angle (and retain) the longitudinal axis 26 of the distal shaft section parallel to (i.e. at 0°) to the longitudinal axis 66 of the additional shaft section 20B (see FIGS. 1A and 1B); and
- the engagement surface 9B can be engaged with the engagement surface 151 of the engagement member 150 to angle (and retain) the longitudinal axis 26 of the distal shaft section 20A at −30° to the longitudinal axis 66 of the additional shaft section 20B (see FIG. 3). Although the present example includes two engagement surfaces 9A, 9B, it is envisaged that a different number of such surfaces may be provided.

To release the engagement surface 151 from the proximal end 24 of the distal shaft section 20A, the engagement member 150 may be retracted in an proximal, axial direction, against the bias provided by the spring 82. The engagement member 150 may include a gripping surface 152 for assisting the surgeon to retract the engagement member 150 manually. When the proximal end 24 (e.g. one of the engagement surfaces 9A, 9B) is released from the engagement surface 151 by retraction of the engagement member 150, the distal shaft section 20A is able freely to pivot about the pivotal connection 170. The surgeon may then angle the distal shaft section 20A as desired (e.g. by presenting a different one of the engagement surfaces 9A, 9B to the engagement surface 151) and then release the engagement member 150 so that the engagement surface 151 re-engages with the proximal end 24 of the distal shaft section 20A under the bias provided by the spring 82.

An acetabular reamer handle according to an embodiment of this invention may be included in a surgical kit. The kit may also include one or more differently sized acetabular reamers 100 connectable to the head part of the driveline of the acetabular reamer handle. A kit incorporating an acetabular reamer handle according to an embodiment of this invention may negate the need to provide a plurality of reamer handles having different configurations. This can reduce the cost, weight and cleaning time of the kit.

In one embodiment, a method of reaming an acetabulum of a patient may include connecting an acetabular reamer 100 to the head part 42 of the driveline 40 of an acetabular reamer handle 10 of the kind described above. The method may also include orienting the neck part 6 and the distal shaft section 20A at a first angle relative to each other. The method may further include orienting the additional shaft section 20A and the distal shaft section 20B at a second angle relative to each other. The method may also include operating the driveline 40 (e.g. by connecting the proximal end 45 of the driveline to a rotational power tool and switching on the rotational power tool) to apply torque to the acetabular reamer 100 while the acetabular reamer 100 is located in the acetabulum of the patient.

Orienting the neck part 6 and the distal shaft section 20A at the first angle relative to each other may include pivoting the neck part 6 to present one of the plurality of engagement surfaces 8A, 8B, 8C located at the proximal end 62 of the neck part 6 with the distally facing engagement surface 51 located at the distal end 22 of the distal shaft section 20A. This may include also manually retracting the engagement member 50 in a proximal direction to disengage the distally facing engagement surface 51 of the distal shaft section 20A from one of the engagement surfaces 8A, 8B, 8C, to allow the neck part 6 to pivot freely with respect to the distal shaft section 20A.

Similarly, orienting the distal shaft section 20A and the additional shaft section 20B at the second angle relative to each other may include pivoting the distal shaft section 20A to present one of the plurality of engagement surfaces 9A, 9B located at the proximal end 24 of the distal shaft section 20A with the distally facing engagement surface 151 located at the distal end 32 of the additional shaft section 20B. This may include also manually retracting the engagement member 150 in a proximal direction to disengage the distally facing engagement surface 151 of the additional shaft section 20B from one of the engagement surfaces 9A, 9B, to allow the distal shaft section 20A to pivot freely with respect to the additional shaft section 20B.

Figure 6:
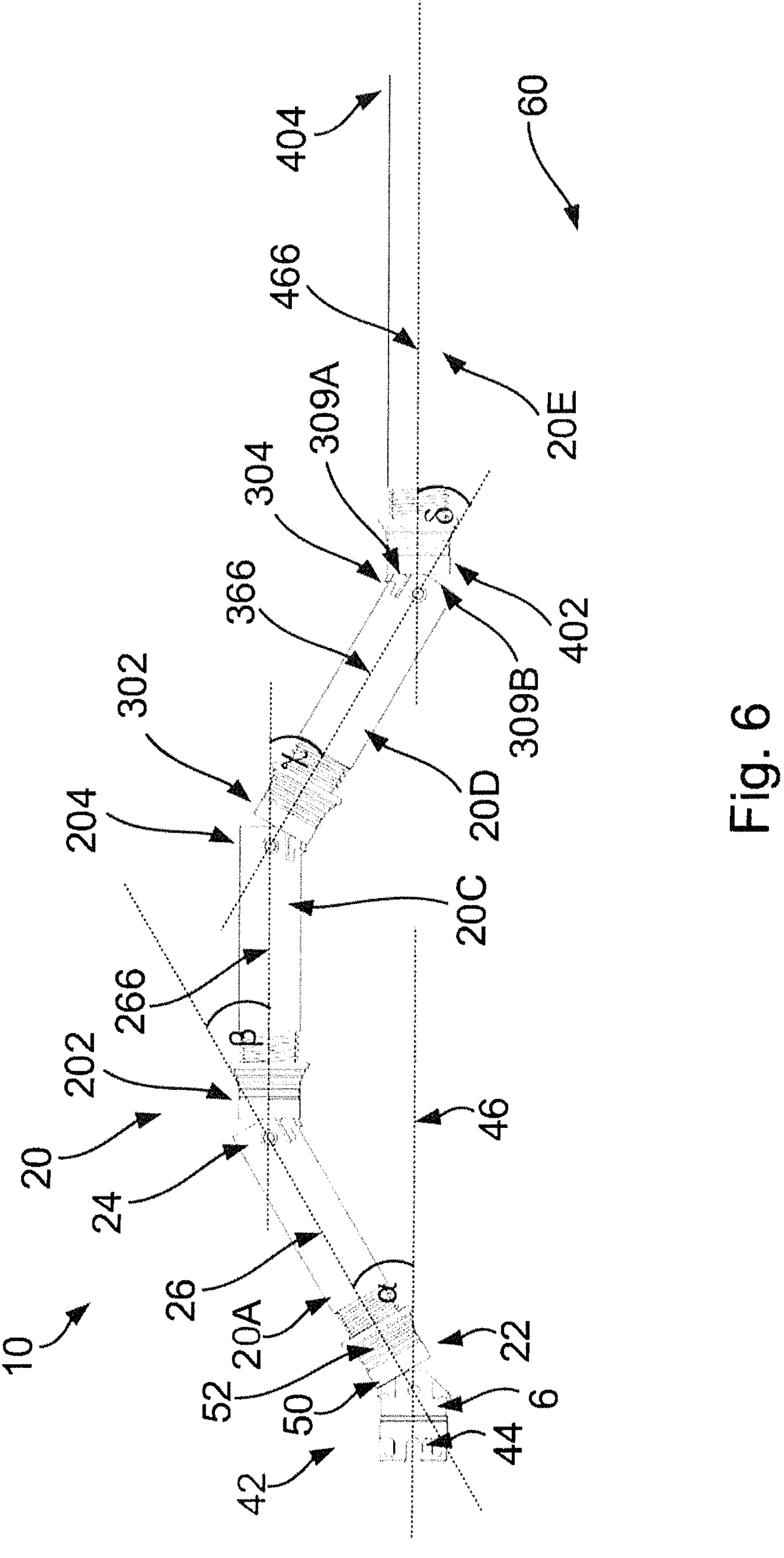
FIG. 6 shows a side view of an acetabular reamer handle according to another embodiment of this invention.

FIG. 6 shows a side view of an acetabular reamer handle 10 according to another embodiment of this invention.

The acetabular reamer handle 10 includes a neck part 6. The neck part 6 in this embodiment is substantially the same as the neck part 6 described above in relation to the embodiment of FIG. 1 and accordingly will not be described here in detail.

In this embodiment, the shaft 20 includes four shaft sections.

These shaft sections include a distal shaft section 20A. The distal shaft section 20A is substantially the same as the distal shaft section 20A described above in relation to the embodiment of FIG. 1 and accordingly will not be described here in detail.

The shaft sections also include a first intermediate shaft section 20C. The first intermediate shaft section 20C has a proximal end 204 and a distal end 202. The distal end 202 is pivotally attached to the proximal end 24 of the distal shaft section 20A. The first intermediate shaft section 20C has a longitudinal axis 266.

The shaft sections further include a second intermediate shaft section 20D. The second intermediate shaft section 20C has a proximal end 304 and a distal end 302. The distal end 302 is pivotally attached to the proximal end 204 of the first intermediate shaft section 20C. The second intermediate shaft section 20D has a longitudinal axis 366.

The shaft sections also include a proximal shaft section 20E. The proximal shaft section 20E has a proximal end 404 and a distal end 402. The distal end 402 of the proximal shaft section 20E is pivotally attached to the proximal end 304 of the second intermediate shaft section 20D. The proximal shaft section 20E has a longitudinal axis 466. Aside from the fact that the proximal shaft section 20E is pivotally attached to the second intermediate shaft section 20D, the proximal shaft section 20E in this embodiment is substantially the same as the additional shaft section 20B which forms the proximal shaft section in the embodiment of FIG. 1.

The acetabular reamer handle 10 in this embodiment includes a driveline. The driveline includes a head part 42. The driveline may be configured in the same way as described above in relation to FIG. 4, with the exception that the driveline in this embodiment includes four driveline sections (i.e. a respective driveline section for each of the shaft sections of the shaft 20). As described above, the driveline sections may be connected together by universal joints that are located at the pivot points between the shaft sections. As with the embodiment of FIG. 1, the proximal end 404 of the proximal shaft section 20E may include an opening through which a proximal end of the driveline may protrude.

In this embodiment, the pivotal attachments (including respective optional locking mechanisms) between:

- the distal shaft section 20A and the first intermediate shaft section 20C;
- first intermediate shaft section 20C and the second intermediate shaft section 20D; and
- the second intermediate shaft section 20D and the proximal shaft section 20E, are all configured in substantially the same way as the pivotal attachment and optional locking mechanism between the distal shaft section 20A and the additional shaft section 20B in the embodiment of FIG. 1. Details of these pivotal attachments and respective locking mechanisms in the present embodiment will therefore not be described here in detail, except to note that the plurality of engagement surfaces 309A, 309B located at the proximal end 304 of the second intermediate shaft section 20D are oriented differentially to the engagement surfaces located at the proximal ends of the distal shaft section 20A and the first intermediate shaft section 20C. This allows the second intermediate shaft section 20D and the proximal shaft section 20E to be pivoted (and then locked) in an opposite direction to the direction in which the other shaft sections of the shaft 20 are pivoted and locked.

In FIG. 6, the pivot angle between the neck part 6 and the distal shaft section 20A is denoted $\alpha$, the pivot angle between the distal shaft section 20A and the first intermediate shaft section 20C is denoted $\beta$, the pivot angle between the first intermediate shaft section 20C and the second intermediate shaft section 20D is denoted $\chi$, and the pivot angle between the second intermediate shaft section 20D and the proximal shaft section 20E is denoted $\delta$.

As described herein, the pivotal connections between the neck part 6 and various shaft sections can allow the acetabular reamer handle 10 to adopt a plurality of different configurations. For instance, it will be appreciated that the acetabular reamer handle 10 of the embodiment of FIG. 6 may be configured as an offset reamer handle (with, by way of example only, $\alpha \neq 0$ (e.g. ±30°, ±45°, ±60°, etc.); $\beta = -\alpha$; and $\chi = \delta = 0$), as a reamer handle including a single bend (with one of $\alpha$, $\beta$, $\chi$ or $\delta$ being non-zero, and the remaining angles equal to zero) and/or as a substantially straight reamer handle having no bends in it ($\alpha=\beta=\chi=\delta=0$).

As shown in FIG. 6, the pivotal connections locking mechanisms between the neck part 6, distal shaft section 20A, first intermediate shaft section 20C, second intermediate shaft section 20D and proximal shaft section 20E in this embodiment can also allow the acetabular reamer handle 10 to adopt a substantially C-shaped configuration. For instance, in one embodiment, it is envisaged that the neck part 6 and the various shaft sections may be arranged (pivoted) such that a $\alpha\neq0$ (e.g. ±30°, ±45°, ±60°, etc.); $\beta=-\alpha$; $\chi=\beta=-\alpha$; $\delta=\alpha$. In such an embodiment, the longitudinal axis 46 of the neck part 6 is oriented substantially parallel to the longitudinal axis 466 of the proximal shaft section 20E.

Accordingly, there has been described an acetabular reamer handle and a method of reaming an acetabulum. The handle includes a hollow shaft having a plurality of shaft sections including a distal shaft section having a distal end and a proximal end and an additional shaft section having a distal end that is pivotally attached to the proximal end of the distal shaft section to allow the additional shaft section and the distal shaft section to be adjustably oriented at an angle. The handle also includes a hollow neck part having a longitudinal axis. The handle further includes a driveline having a head part mounted for rotation about the longitudinal axis and connectable to a reamer. A distal end of the distal shaft section is pivotally attached to a proximal end of the neck part to allow the distal shaft section and the neck part to be adjustably oriented at an angle.

Although particular embodiments of the invention have been described, it will be appreciated that many modifications/additions and/or substitutions may be made within the scope of the claimed invention.

The invention claimed is:

1. An acetabular reamer handle comprising:

a hollow shaft having a plurality of shaft sections comprising:

a distal shaft section having a distal end and a proximal end, the proximal end of the distal shaft section having a plurality of flat engagement surfaces;

an additional shaft section defining a first longitudinal axis and having a distal end that is pivotally attached to the proximal end of the distal shaft section via a first universal joint that provides a first pivot point between the distal end of the additional shaft section and the proximal end of the distal shaft section, wherein the first universal joint allows the additional shaft section and the proximal end of the distal shaft section to be adjustably oriented at an angle relative to each other at the first pivot point; and a first locking mechanism located at the distal end of the additional shaft section and operable to prevent pivotable movement of the distal shaft section relative to the additional shaft section, wherein the first locking mechanism comprises a first tubular engagement member within which the distal end of the additional shaft section is received and a helical spring extending between a proximal end of the first tubular engagement member and a circumferential lip of the additional shaft section, the first tubular engagement member defining a ring-shaped engagement surface on a distal end thereof, wherein the distal shaft section is pivotable with respect to the additional shaft section to present each one of said plurality of flat engagement surfaces of the distal shaft section to the ring-shaped engagement surface for contact therebetween to orient the distal shaft section and the additional shaft section at a respective angle relative to each other, wherein the helical spring is configured to urge the ring-shaped engagement surface of the first tubular engagement member against one of the plurality of flat engagement surfaces of the distal shaft section to lock the distal shaft section at a first angle relative to the additional shaft section, wherein the first angle is selected from a plurality of predetermined angles; and a hollow neck part defining a second longitudinal axis and having a proximal end that is pivotally attached to the distal end of the distal shaft section via a second universal joint that provides a second pivot point between the distal end of the distal shaft section and the proximal end of the neck part, wherein the second universal joint allows the distal end of the distal shaft section and the neck part to be adjustably oriented at an angle relative to each other at the second pivot point, and wherein the first and second pivot points provided by the respective first and second universal joints are configured to be adjustably oriented independent of each other to allow the distal end of the distal shaft section and the neck part to be oriented differently than the proximal end of the distal shaft section and the additional shaft section such that the distal shaft section and the neck part are movable to a first configuration in which the second longitudinal axis of the neck part is parallel and offset from the first longitudinal axis of the additional shaft section and to a second configuration in which the second longitudinal axis of the neck part and the first longitudinal axis of the additional shaft section are coaxial with each other; and a driveline extending through the shaft and the neck part, wherein a head part of the driveline is mounted for rotation about the second longitudinal axis of the neck part and is connectable to an acetabular reamer.

2. The acetabular reamer handle of claim 1, further comprising:

a distally facing engagement surface located at the distal end of the distal shaft section; and a plurality of engagement surfaces located at the proximal end of the neck part, wherein the neck part is pivotable with respect to the distal shaft section to present each one of said plurality of engagement surfaces to the distally facing engagement surface located at the distal end of the distal shaft section to orient the neck part and the distal shaft section at a respective angle relative to each other.

3. The acetabular reamer handle of claim 2, wherein the distally facing engagement surface is provided on a second tubular engagement member, wherein the second tubular engagement member is resiliently biased distally to urge the distally facing engagement surface against one of the plurality of engagement surfaces located at the proximal end of the neck part to resist relative movement between the neck part and the distal shaft section.

4. The acetabular reamer handle of claim 2, wherein the distally facing engagement surface and each of the plurality of engagement surfaces located at the proximal end of the neck part are substantially flat.

5. The acetabular reamer handle of claim 1, wherein the first tubular engagement member of the first locking mechanism is resiliently biased distally to urge the ring-shaped engagement surface against one of said plurality of flat engagement surfaces located at the proximal end of the distal shaft section to resist relative movement between the distal shaft section and the additional shaft section.

6. The acetabular reamer handle of claim 5, wherein the first tubular engagement member is proximally retractable along the first longitudinal axis of the additional shaft section for disengaging the ring-shaped engagement surface from one of the plurality of flat engagement surfaces located at the proximal end of the distal shaft section to allow the distal shaft section to pivot freely with respect to the additional shaft section.

7. The acetabular reamer handle of claim 6, wherein the first tubular engagement member includes a gripping surface for allowing a surgeon to manually operate the first tubular engagement member.

8. The acetabular reamer handle of claim 1, wherein:

the distal end of the additional shaft section and the proximal end of the distal shaft section are pivotally attached to allow the additional shaft section and the distal shaft section to be adjustably oriented at an angle relative to each other only within a first plane, and the distal end of the distal shaft section is pivotally attached to the proximal end of the neck part to allow the distal shaft section and the neck part to be adjustably oriented at an angle relative to each other only in said first plane.

9. The acetabular reamer handle of claim 1, wherein the shaft includes more than two shaft sections, wherein the additional shaft section is an intermediate shaft section, and wherein the shaft includes one or more further pivotally connected shaft sections arranged proximally of the intermediate shaft section.

10. The acetabular reamer handle of claim 9, wherein said intermediate shaft section forming a first intermediate shaft section and a second intermediate shaft section, wherein a distal end of the second intermediate shaft section is pivotally attached to a proximal end of the first intermediate shaft section; and a further shaft section forming a proximal shaft section of the shaft, wherein a distal end of the proximal shaft section is pivotally attached to a proximal end of the second intermediate shaft section.

11. A surgical kit comprising the acetabular reamer handle of claim 1 and one or more differently sized acetabular reamers connectable to the head part of the driveline of the acetabular reamer handle.

12. The acetabular reamer handle of claim 1, further comprising: a second locking mechanism located at the distal end of the distal shaft section and operable to prevent pivotable movement of the neck part relative to the distal end of the distal shaft section, wherein the second locking mechanism comprises a second tubular engagement member within which the distal end of the distal shaft section is received and a second helical spring extending between a proximal end of the second tubular engagement member and a circumferential lip of the distal shaft section, wherein the second helical spring is configured to urge a distal end of the second tubular engagement member against the proximal end of the hollow neck part to lock the neck part at a second angle relative to the distal end of the distal shaft section, wherein the second angle is selected from a plurality of predetermined angle.

13. A method of reaming an acetabulum of a patient, the method comprising:

connecting a reamer to a head part of a driveline of an acetabular reamer handle, the acetabular reamer handle comprising:

a hollow shaft having a plurality of shaft sections comprising:

a distal shaft section having a distal end and a proximal end, the proximal end of the distal shaft section having a plurality of flat engagement surfaces;

an additional shaft section defining a first longitudinal axis and having a distal end that is pivotally attached to the proximal end of the distal shaft section via a first universal joint at a first pivot point between the distal end of the additional shaft section and the proximal end of the distal shaft section; and a first locking mechanism located at the distal end of the additional shaft section and operable to prevent pivotable movement of the distal shaft section relative to the additional shaft section, wherein the first locking mechanism comprises a first tubular engagement member within which the distal end of the additional shaft section is received and a first helical spring extending between a proximal end of the first tubular engagement member and a circumferential lip of the additional shaft section, the first tubular engagement member defining a ring-shaped engagement surface on a distal end thereof, wherein the distal shaft section is pivotable with respect to the additional shaft section to present each one of said plurality of flat engagement surfaces of the distal shaft section to the ring-shaped engagement surface for contact therebetween to orient the distal shaft section and the additional shaft section at a respective angle relative to each other, wherein the first helical spring is configured to urge the ring-shaped engagement surface of the first tubular engagement member against one of the plurality of flat engagement surfaces of the distal shaft section to lock the distal shaft section at a first angle relative to the additional shaft section, wherein the first angle is selected from a plurality of predetermined angles;

a hollow neck part having a proximal end that is pivotally attached to the distal end of the distal shaft section via a second universal joint located at a second pivot point between the distal end of the distal shaft section and the proximal end of the neck part and further having a second longitudinal axis, and a second locking mechanism located at the distal end of the distal shaft section and operable to prevent pivotable movement of the neck part relative to the distal end of the distal shaft section, wherein the second locking mechanism comprises a second tubular engagement member within which the distal end of the distal shaft section is received and a second helical spring extending from a proximal end of the second tubular engagement member, wherein the second helical spring is configured to urge a distal end of the second tubular engagement member against the proximal end of the hollow neck part to lock the neck part at a second angle relative to the distal end of the distal shaft section, wherein the second angle is selected from a plurality of predetermined angles, and wherein the first and second pivot points provided by the respective first and second universal joints are configured to be adjustably oriented independent of each other to allow the distal end of the distal shaft section and the neck part to be oriented differently than the proximal end of the distal shaft section and the additional shaft section such that the distal shaft section and the neck part are movable to a first configuration in which the second longitudinal axis of the neck part is parallel and offset from the first longitudinal axis of the additional shaft section and to a second configuration in which the second longitudinal axis of the neck part and the first longitudinal axis of the additional shaft section are coaxial with each other; and said driveline, wherein the driveline extends through the shaft and the neck part, wherein the head part is mounted for rotation about the second longitudinal axis of the neck part, orienting the neck part and the distal shaft section at a first angle relative to each other via the second universal joint at the second pivot point;

orienting the additional shaft section and the distal shaft section at a second angle relative to each other via the first universal joint at the first pivot point; and operating the driveline to apply torque to the reamer while the reamer is located in the acetabulum of the patient.

14. The method of claim 13, wherein orienting the neck part and the distal shaft section at said first angle relative to each other comprises pivoting the neck part to present one of a plurality of engagement surfaces located at the proximal end of the neck part with a distally facing engagement surface located at the distal end of the distal shaft section.

15. The method of claim 14, wherein the distally facing engagement surface is provided on the second tubular engagement member, wherein the second tubular engagement member is resiliently biased distally to urge the distally facing engagement surface against one of said plurality of engagement surfaces located at the proximal end of the neck part to resist relative movement between the neck part and the distal shaft section, and wherein the method further comprises manually retracting the second tubular engagement member in a proximal direction to disengage the distally facing engagement surface from one of the engagement surfaces located at the proximal end of the neck part to allow the neck part to pivot freely with respect to the distal shaft section.

16. The method of any of claim 13, wherein orienting the additional shaft section and the distal shaft section at said second angle relative to each other comprises pivoting the distal shaft section to present one of the plurality of flat engagement surfaces located at the proximal end of the distal shaft section with the ring-shaped engagement surface.

17. The method of claim 16, wherein the first tubular engagement member is resiliently biased distally to urge the ring-shaped engagement surface against one of said plurality of flat engagement surfaces located at the proximal end of the distal shaft section to resist relative movement between the additional shaft section and the distal shaft section, and wherein the method further comprises manually retracting the first tubular engagement member in a proximal direction to disengage the ring-shaped engagement surface from one of the flat engagement surfaces located at the proximal end of the distal shaft section to allow the additional shaft section to pivot freely with respect to the distal shaft section.

18. The method of any of claim 13, comprising: orienting the additional shaft section and the distal shaft section at said first angle relative to each other within a first plane, and orienting the distal shaft section and the neck part at said second angle relative to each other in said first plane.

19. The method of claim 18, wherein the first angle is equal and opposite to the second angle within said first plane.

* * * * *